(12) United States Patent
Park et al.

(10) Patent No.: US 9,382,565 B2
(45) Date of Patent: Jul. 5, 2016

(54) GENERATION OF NUCLEIC ACID MOLECULES

(75) Inventors: Daniel Jonathan Park, Clifton Hill (AU); Karl Frederick Poetter, Northcote (AU); Zaheer Khan, Papatoetoe Manukau (NZ)

(73) Assignee: GENERA BIOSYSTEMS LIMITED, Scoresby Victoria (AU)

( * ) Notice: Subject to any disclaimer, the term of this patent is extended or adjusted under 35 U.S.C. 154(b) by 584 days.

(21) Appl. No.: 12/525,667

(22) PCT Filed: Feb. 1, 2008

(86) PCT No.: PCT/AU2008/000120
§ 371 (c)(1),
(2), (4) Date: Apr. 20, 2010

(87) PCT Pub. No.: WO2008/092213
PCT Pub. Date: Aug. 7, 2008

(65) Prior Publication Data
US 2010/0209971 A1    Aug. 19, 2010

(30) Foreign Application Priority Data

Feb. 2, 2007 (AU) ............................... 2007900508
Aug. 17, 2007 (AU) ............................... 2007904458

(51) Int. Cl.
*C12Q 1/68* (2006.01)
*C12P 19/34* (2006.01)

(52) U.S. Cl.
CPC ................. *C12P 19/34* (2013.01); *C12Q 1/686* (2013.01)

(58) Field of Classification Search
CPC .... C12Q 1/686; C12Q 2565/501; C12P 19/34
See application file for complete search history.

(56) References Cited

U.S. PATENT DOCUMENTS

| 6,277,604 B1 | 8/2001 | Peponnet | |
| 7,273,730 B2 * | 9/2007 | Du Breuil Lastrucci | .... 435/91.2 |
| 7,579,154 B2 * | 8/2009 | Chun | ........................... 435/6.12 |
| 2001/0036632 A1 * | 11/2001 | Yu et al. | .............................. 435/6 |
| 2004/0048270 A1 | 3/2004 | Zeltz et al. | |
| 2007/0003966 A1 * | 1/2007 | Dey et al. | ........................... 435/6 |

FOREIGN PATENT DOCUMENTS

WO          WO 01/85988 A1     11/2001

OTHER PUBLICATIONS

Khan, Z. et al. 2008 "Enhanced solid phase PCR: mechanisms to increase priming by solid support primers" *Analytical Biochemistry* 375(2):391-393.
Mitterer, G. and Schmidt, W.M. 2006 "Microarray-Based Detection of Bacteria by On-Chip PCR" *Methods in Molecular Biology* 345:37-51.
Extended European search report dated Mar. 18, 2010.
Sanchez J.A. et al. 2004 "Linear-After-The-Exponential (LATE)—PCR: An advanced method of asymmetric PCR and its uses in quantitative real-time analysis" *Proc Natl Aced Sci USA* 101: 1933-1938.

* cited by examiner

*Primary Examiner* — Young J Kim

(74) *Attorney, Agent, or Firm* — Knobbe, Martens, Olson & Bear, LLP

(57) ABSTRACT

The present invention relates generally to methods for generating single stranded nucleic acid molecules following enhanced solid phase polynucleotide amplification. The present invention employs an amplification reaction using primers with differential priming properties at particular annealing conditions or an immobilized primer nested between two aqueous phase primers. Thus, by primer design, solid support primer participation is enhanced relative to aqueous phase primers. The subject invention further provides methods for labeling solid matrices with single and double stranded nucleic acid molecules. Kits for generating single stranded nucleic acid molecules and for conducting amplification reactions also form part of the present invention. The present invention further provides amplification systems for the generation of single stranded nucleic acid molecules optionally labelled with a reporter molecule and their use inter alia as labels, primers and probes.

9 Claims, 3 Drawing Sheets

(A)

(B)

GENERATION OF NUCLEIC ACID MOLECULES

RELATED APPLICATIONS

This application is a U.S. National Phase of International Application No.: PCT/AU2008/000120, filed Feb. 1, 2008, designating the U.S. and published in English on Aug. 7, 2008 as WO 2008/092213, which claims the benefit of Australian patent application No. 2007900508, filed Feb. 2, 2007 and Australian patent application No. 2007904458, filed Aug. 17, 2007.

FIELD

The present invention relates generally to methods for generating single stranded nucleic acid molecules following enhanced solid phase polynucleotide amplification. The subject invention further provides methods for labeling solid matrices with single and double stranded nucleic acid molecules. Kits for generating single stranded nucleic acid molecules and for conducting amplification reactions also form part of the present invention. The present invention further provides amplification systems for the generation of single stranded nucleic acid molecules optionally labeled with a reporter molecule and their use inter alia as labels, primers and probes.

BACKGROUND

Reference to any prior art in this specification is not and should not be taken as an acknowledgment or any form of suggestion that this prior art forms part of the common general knowledge in any country.

Double-stranded DNA (dsDNA) can be converted to a single-stranded DNA (ssDNA) by separating the strands or by removing one strand of the duplex. Strands of the duplex can be separated by thermal or chemical means of disrupting interstrand bonds. Removal of one strand permits recovery of the desired strand and elimination of its complement e.g. Nikiforov et al. (U.S. Pat. No. 5,518,900), who described modifying one of two primers used for amplification by incorporation of phosphorothiate nucleotide derivatives in the 5' end of the modified primer, rendering it resistant to exonuclease digestion. After amplifying target sequences using the polymerase chain reaction (PCR), the dsDNA is subjected to exonuclease digestion. The unprotected strand is preferentially digested by a 5' to 3' exonuclease, leaving a single-stranded product consisting of the other strand. Similar strategies have used exonuclease-resistant branched primers (Shchepinov et al, *Nuc. Acids. Res.* 25:4447-4454 1997) or 5' phosphate-bearing substrate preference of Lambda exonuclease (Higuchi et al, *Nucl. Acids Res.* 25:5685, 1989).

Asymmetric PCR (Gyllensten and Erlich, *Proc. Natl. Acad. Sci. USA* 85:7652-7656 1998; U.S. Pat. No. 5,066,584) generates ssDNA during thermocycling by employing an imbalanced primer pair concentration such that one primer is at a limiting concentration. This favours ssDNA product primed by the primer in excess. This approach has the problem of being inherently limited in processivity, since, by necessity, one primer is used at a relatively low concentration.

Competitor primer asymmetric PCR (Gillespie, 1997; U.S. patent application Ser. No. 08/628,417) employs the separate addition of competitor primer following PCR thermocycling and prior to further thermocycling to generate ssDNA. As such, this method requires excessive handling which is undesirable particularly in a diagnostic context due to increased risk of contamination, user error and processing time and cost.

Kaltenboeck et al, *Biotechniques* 12:164-171, 1992 described a method of producing ssDNA by initially performing a PCR to generate dsDNA, followed by a separate reaction using the product of the first PCR as a template for a second linear amplification employing one primer. Again, this method requires excessive handling.

Solid phase matrices have been labeled with PCR products using symmetric PCR or asymmetric PCR where one primer is conjugated to a solid surface or via a 'bridge' PCR where forward and reverse primers are directly conjugated to a solid surface. Each of these approaches is relatively inefficient due to kinetic constraints (low effective substrate concentrations with or without competitive inhibitory effects). If required, dsDNA products conjugated to a solid phase can be converted relatively simply to ssDNA products conjugated to the solid phase by chemical or thermal denaturation.

U.S. Pat. No. 6,277,604 describes the use of an immobilized and two aqueous phase primers in asymmetric PCR. At least one of the aqueous primers is provided in limiting concentration to facilitate the immobilized primer priming an extension event. However, this can lead to inefficiencies.

There is a clear need to develop more efficient methods for generating specific single stranded nucleic acid molecules and to label solid supports.

SUMMARY

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The present invention defines a process for generating single stranded (ss) polynucleotides and in particular specific ssDNA molecules and enhancement of solid phase polynucleotide amplification. Even more particularly, the present invention employs an amplification reaction using primers with differential priming properties at particular annealing conditions. Following a period of exponential amplification in the presence of permissive annealing conditions, the annealing conditions are altered to facilitate differential priming resulting in the efficient generation of a ssDNA or nucleotide analog containing forms thereof. Differential primer annealing properties may also occur by particular primer design offering kinetic advantages or both permissive/non-permissive annealing and primer design. Hence, by primer design, solid support primer participation in priming is enhanced relative to aqueous phase primers. Therefore, asymmetric amplification with compromized sensitivity is not necessary to achieve high loads of amplicon on the solid support. The present invention facilitates uncompromized and more sensitive solid phase amplification. High loading of amplicon-associated signal on the solid support is achieved. The methods of the present invention can be performed in the amplification reaction vessel without need for additional sample handling or processing. Conveniently, although not necessarily, at least one of the primers is labeled with a reporter molecule capable of providing an identified signal.

The method herein is referred to as Enhanced Solid Phase-PCR ("ESP-PCR").

The present invention contemplates, therefore, a method for solid phase amplification of nucleic acids which comprises contacting a solid support having a primer bound to the solid support via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of said immobilized primer.

Reference to "nested" in the context of primers includes fully and partially nested primers. The resulting immobilized nucleic acid may be ss or ds. The immobilized ds nucleic acid molecule may then undergo denaturation to generate either or both of an immobilized ss nucleic acid molecule or an aqueous phase ss nucleic acid molecule.

According to another aspect, the present invention provides a method for generating a single stranded polynucleotide in a reaction vessel, said method comprising subjecting a target double stranded polynucleotide or its single stranded derivative to exponential amplification by contacting a solid matrix having a primer bound to said solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of said immobilized primer to facilitate the generation of double stranded polynucleotide immobilized to the solid matrix and then subjecting the immobilized polynucleotide to denaturing conditions to generate immobilized single stranded polynucleotides and a liquid phase single stranded polynucleotide.

The amplification reaction may be symmetric, asymmetric, polymerase chain reaction (PCR), strand displacement amplification (SDA), ligase-chain reaction, nicking restriction endonuclease (nicking RE), SDA or whole genome amplification, amongst others. Conveniently, at least one of the aqueous phase primers is labeled with a reporter molecule capable of providing an identifiable signal.

The above method is a form of a stepped amplification reaction referred to herein as ESP-PCR. The stepped scheme may be "step up" or "step down" depending on the first and second annealing conditions or primer design. Examples of differential annealing conditions include different annealing temperatures, extent of mismatch between the primer and target complementary polynucleotide, the presence of extraneous or supplementary sequences and primer design within different sites of complementarily on a target nucleotide sequence. In an embodiment, one or both of the primers carries a "heel" or "head" nucleotide sequence which may or may not be related by homology to the target polynucleotide sequence providing a different melting temperature compared to the other primer.

The present invention may also be conducted, therefore, using primers carrying one or more extraneous or supplementary sequences to assist in reducing nucleic acid amplification bias.

The process of the present invention has a range of applications underlying the generation of probes for hybridization reactions (such as Northern blots, Southern blots, clone library screening, in situ hybridization, fluorescence in situ hybridization (FISH) and microarray (eg chip, bead or other solid matrix based analyzes). The instant method may also be used in conjunction with another modified amplification process where a dsDNA target is subjected to 5' to 3' exonuclease digestion to generate a ssDNA template for use in the present process.

The subject invention further contemplates a method for direct polynucleotide labeling of solid phase matrices such as in microarray feature generation, microtiter plate labeling for non-gel electrophoretic based nucleic acid analyses, bead labeling for non-gel electrophoretic based generic analyses (eg FACS-based generic analyses) and in emulsion PCR prior to high through put sequencing regimes or bead microarray applications. Kits comprising reaction vessel and reagents also part of the present invention. "Labeling" includes labeling with a reporter molecule such as a chemiluminesence molecule or bioluminescence molecule and/or labeling with a nucleic acid molecule.

Hence, the present invention is also directed to amplification systems comprising a reagent component, a nucleic acid component, a hardware component and an instructional component. The components of the system interact with each other to generate a single stranded polynucleotide product.

The present invention is also useful in the direct polynucleotide labeling of solid phase matrices such as in a microarray or solid array feature generation microtiter plate labeling for non-gel based nucleic acid analyses (eg FACS-based genetic analyses) and in emulsion amplification prior to high through put sequencing regimes or bead microarray applications. The present invention may also be used to generate ss nucleic acid molecules either immobilized to a solid support or in aqueous phase after denaturing immobilized ds nucleic acid molecules.

Hence, in one particular embodiment, the present invention contemplates a method for labeling a solid matrix with a single stranded polynucleotide, the method comprising subjecting a target double stranded polynucleotide or its single stranded derivative to exponential amplification using forward and reverse primers having similar annealing properties at a first set of annealing conditions but differential annealing properties at a second set of annealing conditions, contacting the amplification product of the amplification with a solid matrix or composition of solid matrices having immobilized thereon at least one of the primers which is capable of annealing to a strand of the amplification product under the second set of annealing conditions and altering the annealing conditions to the second set of conditions to thereby facilitate amplification based on a single primer to generate a single stranded polynucleotide immobilized to the solid matrix.

In another embodiment, the present invention provides a method for labeling a solid matrix with a single stranded polynucleotide, the method comprising subjecting a target double stranded polynucleotide or its single stranded derivative to exponential amplification using forward and reverse primers having similar annealing properties at a first set of annealing conditions but differential annealing properties at a second set of annealing conditions, contacting the amplification product of the amplification with a solid matrix or composition of solid matrices having immobilized thereon at least one of the primers which is capable of annealing to a strand of the amplification product under the second set of annealing conditions generating double stranded polynucleotide and then denaturing the double stranded polynucleotide to generate a single stranded polynucleotide immobilized to the solid matrix.

A method is also provided for labeling a solid matrix which comprises contacting a solid matrix having a primer bound to the solid matrix via linker means with a sample comprising at least one nucleic acid molecule wherein the immobilized primer is selected from the list consisting of:

(i) a primer sharing sequence identity to an aqueous phase primer but having a different melting temperature relative to the immobilized primer; and
(ii) a primer nested between two aqueous phase primers; under reaction conditions which effect elongation of the immobilized primer.

Reference to a "solid matrix" includes a solid phase, support or other surface or bead to which a nucleic acid molecule can be immobilized.

The above methods include the option of altering the annealing condition to the first set of conditions to enable a "filling in" of the single strand polynucleotide to generate double stranded polynucleotides immobilized to the solid matrix.

The present invention extends, therefore, to a method for generating a solid matrix or composition of solid matrices labeled with double stranded polynucleotides, said method comprising subjecting a target double stranded polynucleotide or its single stranded derivative to exponential amplification using forward and reverse primers having similar annealing properties at a first set of annealing conditions but differential annealing properties at a second set of annealing conditions, contacting the product of the amplification with a solid matrix or composition of solid matrixes having immobilized thereon at least one of the primers which is capable of annealing to a strand of the amplification product under the second set of annealing conditions and altering the annealing conditions to the second set to thereby facilitate amplification based on a single primer to generate a single stranded polynucleotide immobilized to said solid matrix; altering to the first set of annealing conditions whereby in the presence of the other primer, the single stranded immobilized polynucleotide generates a complementary strand and the solid matrix comprises an immobilized duplex polynucleotide.

In a further embodiment, the duplex polynucleotide is denatured such as by chemical thermal means to generate aqueous phase single stranded polynucleotide or immobilized single stranded polynucleotide.

A method is also provided for generating a solid matrix or composition of solid matrices labeled with double stranded polynucleotides, the method comprising subjecting a target double stranded polynucleotide or its single stranded derivative to exponential amplification by contacting a solid matrix having a primer bound to said solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers; under reaction conditions which effect elongation of the immobilized primer.

Nested primers together with permissive and non-permissive conditions may also be employed.

Abbreviations used in this specification are defined in Table 1.

TABLE 1

| Abbreviation | Definition |
| --- | --- |
| dsDNA | Double stranded DNA |
| FACS | Fluorescence activated cell sorting |
| FISH | Fluorescence in situ hybridization |

TABLE 1-continued

| Abbreviation | Definition |
| --- | --- |
| PCR | Polymerase chain reaction |
| SDA | Strand displacement amplification |
| ssDNA | Single stranded DNA |

A summary of the sequence identifiers used herein are shown in Table 2.

TABLE 2

| Sequence Identifier | Sequence |
| --- | --- |
| SEQ ID NO: 1 | Oligonucleotide (Transprobe) |
| SEQ ID NO: 2 | Cto3 template generation forward primer |
| SEQ ID NO: 3 | Cto3 template generation reverse primer |
| SEQ ID NO: 4 | Ngo template generation forward primer |
| SEQ ID NO: 5 | Ngo template generation reverse primer |
| SEQ ID NO: 6 | Ngps template generation forward primer |
| SEQ ID NO: 7 | Ngps template generation reverse primer |
| SEQ ID NO: 8 | Cto3 'aqueous' forward primer |
| SEQ ID NO: 9 | Cto3 'aqueous' reverse primer |
| SEQ ID NO: 10 | Cto3 SP-PCR solid support primer |
| SEQ ID NO: 11 | Cto3 ESP-PCR solid support primer |
| SEQ ID NO: 12 | Ngo 'aqueous' forward primer |
| SEQ ID NO: 13 | Ngo 'aqueous' reverse primer |
| SEQ ID NO: 14 | Ngo SP-PCR solid support primer |
| SEQ ID NO: 15 | Ngo ESP-PCR solid support primer |
| SEQ ID NO: 16 | Ngps 'aqueous' forward primer |
| SEQ ID NO: 17 | Ngps 'aqueous' reverse primer |
| SEQ ID NO: 18 | Ngps SP-PCR solid support primer |
| SEQ ID NO: 19 | Ngps ESP-PCR solid support primer |
| SEQ ID NO: 20 | *Neisseria gonorrhoeae* opa primer |
| SEQ ID NO: 21 | *Neisseria gonorrhoeae* opa reverse primer |
| SEQ ID NO: 22 | *Chlamydia trachomatis* cryptic plasmid orf3 primer |
| SEQ ID NO: 23 | *Chlamydia trachomatis* reverse primer. |

BRIEF DESCRIPTION OF THE FIGURES

Some figures contain color representations or entities. Color photographs are available from the Patentee upon request or from an appropriate Patent Office. A fee may be imposed if obtained from a Patent Office.

Figure 1I:
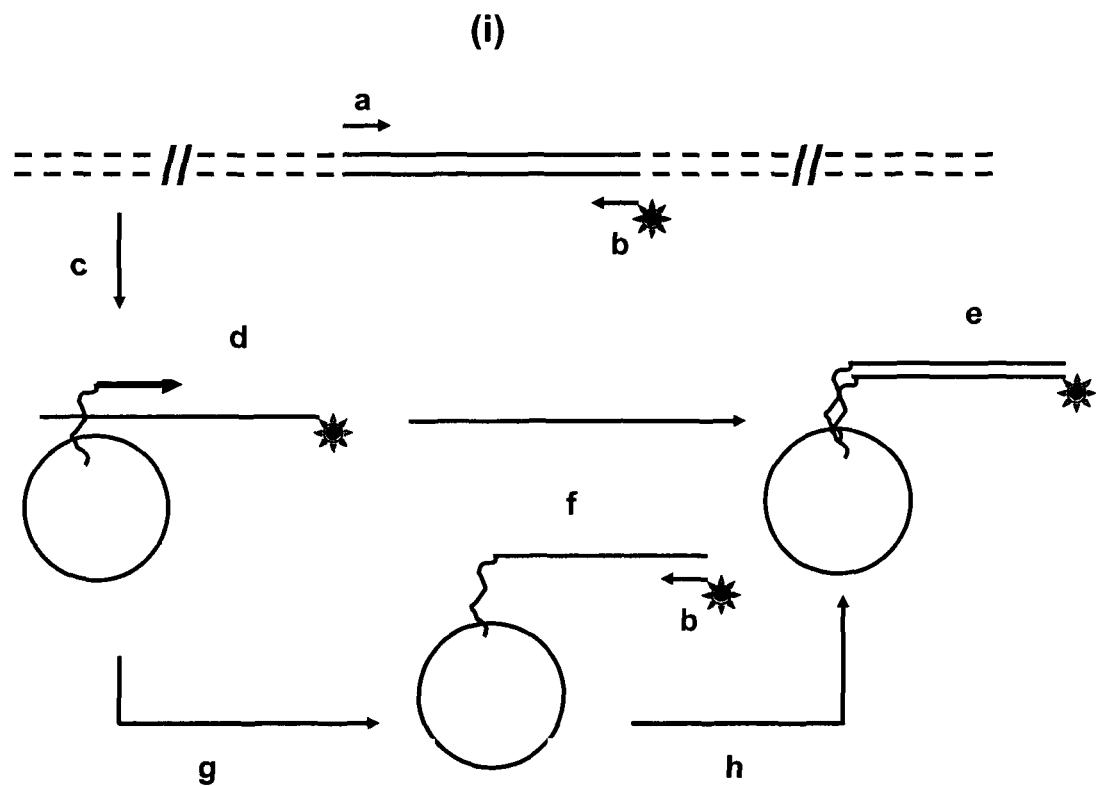
FIGS. 1(*i*) and (*ii*) are diagrammatical representations of (i) Enhanced Solid Phase-PCR (ESP-PCR) Scheme for the loading of single or double stranded amplicons onto a solid support with (ii) solid support primer designs (1 to 4). Refer to Example 1 for a detailed description. (i): a—represents 'forward' PCR primer; b—represents 'reverse' primer; c—exponential amplification using eg. forward and reverse primers (eg. PCR); d—solid support primer [see (ii)]; e—many ds copies/solid support; f—many ss copies/solid support; g—(optional) cycles with 'stepped' annealing conditions non-permissive to primers a and b; h—(optional) 'fill-in'; (ii): a—represents 'forward' PCR primer; b—represents 'reverse' primer; c—prior art solid phase PCR solid support primer design; d—eg. 3-prime extension, higher Tm; e—enhanced solid phase PCR solid support primer designs; f—eg. nested or partially nested; g—eg. nested or partially nested, higher Tm.

(A) solid support priming in standard SP-PCR solid support primer sequence matches its counterpart 'aqueous' primer; (a)—solid support primer priming is outcompeted by its 'aqueous' primer counterpart; (b)—single-stranded amplicon; (B) solid support priming in ESP-PCR primers are nested to reduce competition between it and 'aqueous' primer for binding to amplicon by taking advantage of a different binding site and the lag between 'aqueous' primer binding and polymerase binding. there is also a higher $T_m$, to raise its effective concentration (a)—solid support primer priming is competitive; (b)—single-stranded amplicon.

DETAILED DESCRIPTION

The present invention is directed to a modified amplification reaction which facilitates the generation of single stranded (ss) polynucleotides and in particular ssDNA immobilised to a solid support or in immobilized or aqueous form generated from immobilized stranded (ds) polynucleotides. The present invention is predicated in part of the use of primers in an amplification reaction which have similar annealing characteristics at one set of annealing conditions (wherein the primers are considered "balanced" and the annealing conditions are considered "mutually permissive") and a different or differential or dissimilar annealing characteristics at another set of annealing conditions (wherein the primers are considered "unbalanced" and the annealing conditions are considered "differentially permissive"). Alternatively, or in addition, the different annealing conditions arise from primer design enabling different kinetic advantages for solid support priming over aqueous phase oligonucleotide priming.

Hence, one aspect of the present invention contemplates a method for solid phase amplification of which comprises contacting a solid support having a primer bound to the solid support via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of the immobilized primer.

Reference to "nested" in the context of primers includes fully and partially nested primers.

Reference to "sharing sequence identity" includes substantial identity as well as at least 80% sequence identity such as at least 80, 81, 82, 83, 84, 85, 86, 87, 88, 89, 90, 91, 92, 93, 94, 95, 96, 97, 98, 99 or 100% identity.

As indicated above, the forward and reverse primers can be described as "balanced" or "unbalanced" with respect to the anneal properties and the annealing conditions are regarded as mutually permissive or differentially permissive with respect to the effect on the primers. Similarly, primer design may facilitate differentially permissive primers.

Hence, the balanced or unbalanced primers means that at a given set of conditions or set of primers, i.e. mutually permissive annealing conditions or mutually permissive primers, both primers bind or otherwise hybridize to form a duplex with similar efficiency.

Whereas at differentially permissive annealing conditions (i.e. at an alternative set of conditions), the primers are unbalanced since the conditions may favor duplex formations and priming.

Accordingly, the present invention may be further defined as a method for generating a single stranded polynucleotide immobilized to a solid support in a reaction vessel, the method comprising conducting an amplification reaction of a target polynucleotide immobilized to a solid support in the vessel using a pair of balanced forward and reverse primers at mutually permissive conditions and then altering the annealing conditions to differentially permissive conditions whereby the primers become unbalanced and continuing the reaction to generate single stranded polynucleotide product and then inactivating polymerase activity to substantially prevent formation of double stranded polynucleotides.

In an alternative embodiment, ds polynucleotide is generated onto the solid support which is then subjected to denaturing conditions (e.g. by chemical or thermal means) to generate immobilized ss polynucleotide or aqueous phase polynucleotide.

The present invention provides, therefore, a method for labeling a solid matrix with a single stranded polynucleotide, the method comprising subjecting a target double stranded polynucleotide or its single stranded derivative to exponential amplification using forward and reverse primers having similar annealing properties at a first set of annealing conditions but differential annealing properties at a second set of annealing conditions, contacting the amplification product of the amplification with a solid matrix or composition of solid matrices having immobilized thereon at least one of the primers which is capable of annealing to a strand of the amplification product under the second set of annealing conditions generating double stranded polynucleotide and then denaturing the double stranded polynucleotide to generate a single stranded polynucleotide immobilized to the solid matrix.

Denaturing may be by any means including chemical means or thermal means.

Another aspect provides a method for generating a single stranded polynucleotide in a reaction vessel, said method comprising subjecting a target double stranded polynucleotide or its single stranded derivative to exponential amplification by contacting a solid matrix having a primer bound to said solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of said immobilized primer to facilitate the generation of double stranded polynucleotide immobilized to the solid matrix and then subjecting the immobilized polynucleotide to denaturing conditions to generate immobilized single stranded polynucleotides and a liquid phase single stranded polynucleotide.

An additional step of subjecting the resulting mixture to phase separation means may then also occur.

In another embodiment, a method for generating a single stranded polynucleotide in a reaction vessel is provided, the method comprising, contacting a solid matrix having a primer bound to said solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of the immobilized primer.

Preferably, the polynucleotides are DNA hence the present invention is particularly directed to the generation of ssDNA. However, although the starting material is preferably dsDNA, the present invention may also use mRNA which is converted to ds or ssDNA or use ssDNA. Furthermore, dsDNA may be generated on the solid support and then subjected to denaturing conditions to generate immobilized or aqueous phase ssDNA.

Another aspect of the present invention provides a method of generating ssDNA in a reaction vessel, said method comprising conducting an amplification reaction of an immobilized target ssDNA template from a dsDNA or mRNA target in the reaction vessel using a pair of forward and reverse primers having similar (balanced) annealing primers at a first set of annealing conditions (mutually permissive conditions) but differential annealing properties at a second set of annealing conditions (differentially permissive conditions) wherein the amplification is permitted to proceed under the mutually permissive annealing conditions; altering the conditions to differentially permissive conditions to unbalance the primers thereby facilitating linear amplification substantially in the presence of only a single primer to generate ssDNA product; and inactivating any polymerase activity to substantially reduce or prevent dsDNA formation.

Still another aspect of the present invention, a method of generating ssDNA in a reaction vessel, said method comprising contacting a solid matrix having a primer bound to said solid matrix via linker means with a sample in a reaction vessel comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of the immobilized primer.

The differential permissive versus mutually permissive annealing conditions or primers relate, for example, extent of mismatch, presence of "head" or "tail" extraneous nucleotide sequences on the primers, site of hybridization on target template to form duplexes or the presence of other characteristics to enable a step-up or step-down to generate unbalanced primer conditions.

The method of the present invention may be considered a modification of an amplification reaction to generate a particular product. The modification is the use of primers which are differentially or mutually balanced depending on the level of permissiveness of the annealing conditions.

Hence, the present invention contemplates a modified amplification reaction in which forward and reverse primers are employed to exponentially amplify a template single stranded polynucleotide such as ssDNA generated from a double stranded polynucleotide such as dsDNA or generate from mRNA directly or via cDNA wherein the modification comprises selecting primers which have similar annealing characteristics at a first set of annealing conditions and differential annealing characteristics at second set of annealing conditions such that altering the annealing conditions to the second set facilitates amplification in the presence of a single primer resulting in production of substantially single stranded polynucleotide such as ssDNA.

Alternatively, or in addition, primer design is used to nest the immobilized primer between two aqueous phase primers.

The present invention further provides a method for generating a single stranded polynucleotide in a reaction vessel, said method comprising subjecting a target double stranded polynucleotide or its single stranded derivative to exponential amplification by contacting a solid matrix having a primer bound to said solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of said immobilized primer to facilitate the generation of double stranded polynucleotide immobilized to the solid matrix and then subjecting the immobilized polynucleotide to denaturing conditions to generate immobilized single stranded polynucleotides and a liquid phase single stranded polynucleotide.

This aspect of the subject invention addresses the problem of potential amplification bias by incorporating a non-primer binding region 5' extraneous nucleotide sequence conjugated to a 3' template binding region. Such one or both primers incorporates the 5' extraneous sequence (heel sequence) which acts as a clamp to even out the amplification efficiency across amplification homologs. The heel sequence may or may not be related by homology to the target sequence.

Still a further aspect provides a method for generating a single stranded polynucleotide in a reaction vessel, comprising contacting a solid matrix having a primer bound to the solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of the immobilized primer.

Variations on the methods herein include the use of nested primers and differential melting conditions.

The present invention has many applications including the generation single stranded nucleotide probes for use in hybridization reactions such as Northern blots, Southern blots, clone library screening, in situ hybridization, fluorescence in situ hybridization (FISH) and microarray analysis such as using chip, beads or other solid matrices. The primers may also be labeled with a reporter molecule capable of providing an identifiable signal. For example, a fluorescent, phosphorescent, chemiluminescent or radioactive label may be incorporated into a primer. Alternative labels include but are not limited to biotin-dUTP, phycoerythrin-dUTP, fluorescein-dUTP and [$\alpha$-$^{32}$P]-dUTP including all possible isomers thereof. Enzyme based and chemical detection assays may also be employed.

The method of the present invention may also be used in combination with other amplification modifications. For example, an amplification system which employs an exonuclease and in particular a 5' to 3' exonuclease to generate ssDNA template from dsDNA target.

Accordingly, another aspect of the present invention provides a method for generating ssDNA in a reactor vessel, the method comprising obtaining a dsDNA target or a region of a dsDNA target to be amplified wherein said dsDNA comprises either a recessed 5' end or a blunt end, incubating the dsDNA with a 5' to 3' exonuclease together with reagents required for isothermal amplification of DNA wherein the 5' to 3' exonuclease creates a ssDNA template comprising a 3' to 5' ssDNA fragment of each strand of the dsDNA which is used as a template for amplification; conducting an amplification reaction on the ssDNA using a pair of forward and reverse primers having similar (balanced) annealing primers at a first set of annealing conditions (mutually permissive conditions) but differential annealing properties at a second set of annealing conditions (differentially permissive conditions) wherein the amplification is permitted to proceed under the mutually permissive annealing conditions; altering the conditions to differentially permissive conditions to unbalance the primers thereby facilitating linear amplification substantially in the presence of only a single primer to generate ssDNA product; and inactivating any polymerase activity to substantially reduce or prevent dsDNA formation.

Another aspect of the present invention provides a method for generating ssDNA in a reactor vessel, the method comprising obtaining a dsDNA target or a region of a dsDNA target to be amplified wherein said dsDNA comprises either a recessed 5' end or a blunt end, incubating the dsDNA with a 5' to 3' exonuclease together with reagents required for isothermal amplification of DNA wherein the 5' to 3' exonuclease creates a ssDNA template comprising a 3' to 5' ssDNA fragment of each strand of the dsDNA which is used as a template for amplification; and conducting an amplification reaction on the ssDNA by contacting a solid matrix having a primer bound to said solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of the immobilized primer.

Still further, the method described herein may be used in conjunction with methods to reduce amplication bias.

Accordingly, another aspect provides a method for generating a single stranded polynucleotide in a reaction vessel, the method comprising conducting an amplification reaction of a target polynucleotide in the vessel using a pair of forward and reverse primers having similar annealing properties at a first set of annealing conditions but differential annealing properties at a second set of annealing conditions wherein the amplification is permitted to proceed under said first set of annealing conditions; altering the annealing conditions to the second set of annealing conditions to facilitate a linear application substantially in the presence of only one of the primers, in the pair, and then inactivating polymerase activity in the amplification reaction to substantially prevent formation of double stranded polynucleotides wherein the amplification step comprises subjecting a nucleic acid template of said polynucleotide target to amplification using forward and reverse primers wherein at least one primer contains a 5' extraneous nucleotide sequence conjugated to a 3' template binding primer region wherein the extraneous nucleotide sequence is incorporated into an amplification product after initial priming.

This step reduces amplification bias. As indicated above, the 5' extraneous sequence may or may not be related to the target sequence.

The present invention is also useful in the direct polynucleotide labeling of solid phase matrices such as in a microarray or solid array feature generation, microtiter plate labeling for non-gel based nucleic acid analyses, bead labeling for non-gel based genetic analyses (e.g. FACS-based genetic analyses) and in emulsion amplification prior to high throughput sequencing regimes or bead microarray applications.

Hence, in one particular embodiment, the present invention contemplates a method for labeling a solid matrix with a single stranded polynucleotide the method comprising subjecting a target double stranded polynucleotide or its single stranded derivatives to exponential amplification using forward and reverse primers having similar annealing properties at a first set of annealing conditions but differential annealing properties at a second set of annealing conditions; contacting the amplicon product of the amplification with solid matrix or composition of solid matrices having immobilized thereon at least one of the primers which is capable of annealing to a strand of the amplicon product under the second set of annealing conditions and altering the annealing conditions to second set to thereby facilitate amplification based on a single primer to generate a single stranded polynucleotide immobilized to said solid matrix.

The above method may further optionally comprise altering the annealing condition to the first set of conditions to enable "filling in" of the ss polynucleotide to generate ds polynucleotide immobilized to the solid matrix. In other words, the conditions are changed to permissive conditions. Double stranded polynucleotide may then be denatured to generate immobilized and aqueous phase ss polynucleotide.

Hence, the present invention extends to a method for generating a solid matrix or composition of solid matrices labeled with double stranded polynucleotide the method comprising subjecting a target double stranded polynucleotide or its single stranded derivatives to exponential amplification using forward and reverse primers having similar annealing properties at a first set of annealing conditions but differential annealing properties at a second set of annealing conditions; contacting the amplicon produce of the amplification with solid matrix or composition of solid matrices having immobilized thereon at least one of the primers which is capable of annealing to a strand of the amplicon product under the second set of annealing conditions and altering the annealing conditions to second set to thereby facilitate amplification based on a single primer to generate a single stranded polynucleotide immobilized to said solid matrix; altering the annealing conditions to the first set of conditions whereby in the presence of the other primer, the single stranded immobilized polynucleotide generates a complete strand or a strand hybridizing to the immobilized strand to generate a duplex polynucleotide labeled solid matrix.

In a further embodiment, a method is provided for generating a solid matrix or composition of solid matrices labeled with double stranded polynucleotides, said method comprising contacting a solid matrix having a primer bound to said solid matrix via linker means with a sample comprising at least one nucleic acid molecule wherein the immobilized primer is selected from the list consisting of:
(i) a primer sharing sequence identity to an aqueous phase primer but having a different melting temperature relative to the immobilized primer; and
(ii) a primer nested between two aqueous phase primers;
under reaction conditions which effect elongation of said immobilized primer.

In describing the present invention, the following terms and contents are defined or clarified.

All scientific citations, patents, patent applications and manufacturer's technical specifications referred to herein are incorporated by reference in their entirety.

It is understood that unless otherwise indicated, the subject invention is not limited to specific reagents, process steps, or applications or the like, as such may vary. It is also to be understood that the terminology used herein is for the purpose of describing particular embodiments only and is not intended to be limiting.

As used in the subject specification, the singular forms "a", "an" and "the" include plural aspects unless the context clearly dictates otherwise. Thus, for example, reference to "a target" includes a single target, as well as two or more targets; reference to "an amplification" includes a single amplification, as well as multiple amplification steps; reference to "the amplicon" includes a single or multiple or complex amplicons; and so forth.

Terms and symbols of nucleic acid chemistry, biochemistry, genetics, and molecular biology used herein follow those of stranded treatises and texts in the field, e.g. Kornberg and Baker, *DNA Replication*, Second Edition (W.H. Freeman, New York, 1992); Lehninger, Biochemistry, Second Edition (Worth Publishers, New York, 1975); Strachan and Read, *Human Molecular Genetics*, Second Edition (Wiley-Liss, New York, 1999); Eckstein (Ed), *Oligonucleotides and Analogs: A Practical Approach* (Oxford University Press, New York, 1991); Gait (Ed), *Oligonucleotide Synthesis: A Practical Approach* (IRL Press, Oxford, 1984); and the like.

"Amplicon" means the product of a polynucleotide amplification reaction. That is, it is a population of polynucleotides, usually but not necessarily double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to PCR, linear polymerase reactions, NASBAs, rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese Patent Publ. No. JP 4-262799 (rolling circle amplification); and the like.

An amplification reaction may be a "real-time" amplification where detection chemistry permits a reaction product to be measured as the amplification reaction progresses. The amplification may be asymmetric or symmetric amplification.

As used herein, the term "amplifying" means performing an amplification reaction. A "reaction mixture" or "reaction vessel" means a solution or compartment containing all the necessary reactants for performing a reaction, which may include, but not be limited to, buffering agents to maintain pH at a selected level during a reaction, salts, co-factors, scavengers, and the like.

"Complementary or substantially complementary" refers to the hybridization or base pairing or the formation of a duplex between nucleotides or nucleic acids, such as, for instance, between the two strands of a dsDNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when, for example, a DNA strand hybridizes under selective hybridization conditions to its complement. Typically, selective hybridization occurs when there is at least about 65% complementary over a stretch of at least 14 to 25 nucleotides, preferably at least about 75%, more preferably at least about 90% complementary. See, Kanehisa *Nucleic Acids Res.* 12:203, 1984, incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand.

"Genetic locus" or "locus" in reference to a genome or target polynucleotide, means a contiguous subregion or segment of the genome or target polynucleotide. As used herein, genetic locus, or locus, may refer to the position of a gene or portion of a gene in a genome, or it may refer to any contiguous portion of genomic sequence whether or not it is within, or associated with, a gene. Preferably, a genetic locus refers to any portion of genomic sequence from a few tens of nucleotides, e.g. 10-30, or 10-100, in length, to a few hundred nucleotides, e.g. 100-1000 or 100-500 in length, to a few thousands of nucleotides in length, e.g. 1000-10,000 or 1000-3000 in length. In some contexts, genetic loci may refer to the location of a nucleotide within a genome.

"Kit" refers to any delivery system for delivering materials or reagents for carrying out a method of the instant invention. In the context of reaction assays, such delivery systems include systems that allow for the storage, transport, or delivery of reaction reagents (e.g. probes, enzymes, etc. in the appropriate containers) and/or supporting materials (e.g. buffers, written instructions for performing the assay etc.) from one location to another. For example, kits include one or more enclosures (e.g. boxes) containing the relevant reaction reagents and/or supporting materials. Such contents may be delivered to the intended recipient together or separately. For example, a first container may contain an enzyme for use in an assay, while a second container contains probes. The kits may also contain compartments adapted to contain the reagents. In one example, a compartment comprises a solid matrix having oligonucleotides or primers or polynucleotides immobilized thereon which participate in the amplification reaction. An example of a solid matrix is a microarray. A kit, therefore, may be part of an overall amplification system having a reagent component, a nucleic acid component, a hardware component and an instructional component. Reference to a "solid matrix" includes any form of structural confine for performance of an amplification reaction. Hence, emulsion PCR, for example, is regarded as a form of solid matrix where the PCR is conducted in the various phases of the emulsion.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is disclosed in the following references that are incorporated by reference: Schena (Ed), Microarrays: A Practical Approach (IRL Press, Oxford, 2000); Southern, *Current Opin. Chem. Biol.*, 2: 404-410, 1998.

A "random microarray" refers to a microarray whose spatially discrete regions of oligonucleotides or polynucleotides are not spatially addressed. That is, the identity of the attached oligonucleotides or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Likewise, after formation, microbeads, or oligonucleotides thereof, in a random array may be identified in a variety of ways, including by optical labels, e.g. fluorescent dye ratios or quantum dots, shape, sequence analysis, or the like.

"Nucleoside" as used herein includes the natural nucleosides, including 2'-deoxy and T-hydroxyl forms, e.g. as described in Kornberg and Baker, DNA Replication, 2' Ed. (Freeman, San Francisco, 1992).

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al. (Eds), PCR: *A Practical Approach and PCR2: A Practical Approach* (IRL Press, Oxford, 1991 and 1995, respectively). For example, in a conventional PCR using Taq DNA polymerase, a double stranded target nucleic acid may be denatured at a temperature >90° C., primers annealed at a temperature in the range 35-90° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, *Nucleic Acids Research*, 30:1292-1305, 2002, which is also incorporated herein by reference. "Nested PCR" means a two-stage PCR wherein the amplicon of a first PCR becomes the sample for a second PCR using a new set of primers, at least one of which binds to an interior location of the first amplicon.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like.

Whenever a polynucleotide or oligonucleotide is represented by a sequence of letters (upper or lower case), such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or PCRs, employing two or more primers. Guidance for selecting the lengths and sequences of primers for particular applications is well known to those of ordinary skill in the art, as evidenced by the following references that are incorporated by reference: Dieffenbach (Ed), *PCR Primer: A Laboratory Manual*, $2^{nd}$ Edition (Cold Spring Harbor Press, New York, 2003).

"Sample" means a quantity of material from a biological, environmental, medical, or patient source in which detection or measurement of target nucleic acids is sought. On the one hand it is meant to include a specimen or culture (e.g. microbiological cultures). On the other hand, it is meant to include both biological and environmental samples. A sample may include a specimen of synthetic origin. Biological samples may be animal, including human, fluid, solid (e.g. stool) or tissue, as well as liquid and solid food and feed products and ingredients such as dairy items, vegetables, meat and meat by-products, and waste. Biological samples may include materials taken from a patient including, but not limited to, cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

"Solid support", "support", "solid phase support" and "solid matrices" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. As indicated above, an emulsion phase is regarded as a "solid support" or "solid matrix". Microarrays usually comprise at least one planar solid phase support, such as a glass microscope slide. The supports may also be of multiple sizes to allow for sorting.

The nucleic acid molecule/primer on the solid support may be immobilized directly or via a chemical or nucleotide bridge. All such coupling chemistries are encompassed by the term "linker means".

EXAMPLE 1

Stepped Asymmetric PCR Scheme

Figure 1:
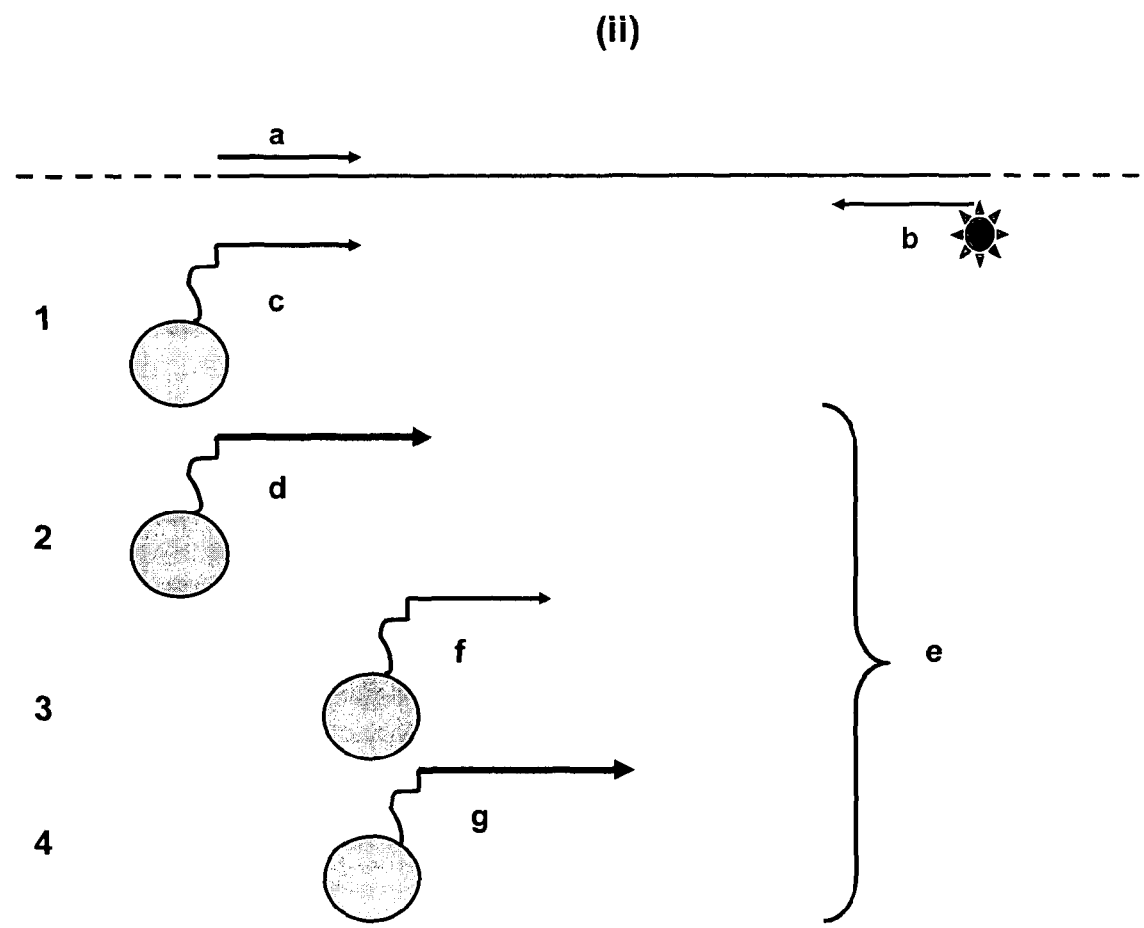

FIG. 1 (*i*) provides a schematic representation of Enhanced Solid Phase PCR for the loading of single or double stranded amplicon onto solid support. A region of DNA to be amplified and amplicons derived from this are depicted by solid lines. Dashed lines represent sequence outside the target region. Primer (depicted by arrow) a represents 'forward' PCR primer and b represents 'reverse' primer. In this example, solid support is represented by a circle. Note that solid support is conjugated to many copies of solid support primer, although for schematic simplicity only one solid support primer is represented. Wavy lines represent non-target-specific linker sequence. Longer, thicker arrows illustrate higher target-specific Tm primers. Primer b has the optional inclusion of a labeling molecule eg. fluor for use in direct detection systems (depicted by star). Labelling molecules could optionally be included as reaction substrates eg. fluor-labeled dNTPs. Primer b is optionally designed such that in a given temperature range, primer b binding to target sequence and priming of polymerase extension from the primer is more efficient than primer a. An example of a design method to achieve this end includes primer b having a higher target-specific melting temperature than primer a such that at increased annealing temperature primer b binds and primes whereas primer a does not. Another example is where primer a exhibits 'panhandle suppression' below a certain temperature, such that below this temperature, primer b binds and primes, whereas primer a does not.

Primer a and primer b are employed as part of a conventional or Asymmetric PCR regimen with the inclusion of solid support primer.

A conventional PCR is performed with the inclusion of primer a, primer b and solid support conjugated primer under thermocycling conditions permissive to all primers. Solid support primer is designed such that in a given temperature range, priming of polymerase extension from the primer is more competitive than primer a. Solid support primer designs depicted in FIG. 1: (ii)2, (ii)3 and (ii)4 offer improved solid support primer participation versus prior art ((ii)1) by virtue of eg. higher Tm and/or being nested or partially nested. Prior art (ii)1 uses target-specific sequence which identically matches the corresponding 'aqueous' primer, along with a 5-prime linker sequence. In the examples illustrated here, (ii)2 includes a 3-prime sequence extension to raise the Tm versus (ii)1, (ii)3 includes target specific sequence that is nested or partially nested with respect to (ii)1 although the target-specific Tm is similar to (ii)1, and (ii)4 includes target specific sequence that is nested or partially nested with respect to (ii)1 and has higher target-specific Tm than (ii)1. These design differences offer kinetic benefits to participation by solid support primer versus prior art, such that solid support loading of amplicon is facilitated.

During latter thermal cycles, optionally, annealing steps can have raised or lowered temperature versus earlier cycles such that solid support primer still anneals to target efficiently but competitor 'aqueous' primer a does not. For example where solid support primer exhibits higher target-specific Tm than primer a, at raised temperatures, solid support primer primes but primer a does not. Another example is where primer a exhibits 'panhandle suppression' below a certain temperature, such that below this temperature, solid support primer binds and primes, whereas primer a does not. Primer b can be designed to have similar priming characteristics to either primer a or solid support primer. Employment of multiple such latter cycles where primer b does not bind to target efficiently enables generation of single stranded solid support amplicon. Employment of such latter cycles where primer b does bind to target efficiently enables generation of double stranded solid support amplicon. Employment of such latter cycles where primer b does not bind to target efficiently, followed by conditions permissive to primer b binding enables generation of double stranded solid support amplicon.

Optionally, double stranded solid support amplicon can subsequently be converted to single stranded solid support amplicon by eg. thermal or chemical denaturation and washing away the solution phase or eg. exonuclease processing.

EXAMPLE 2

Solid Phase Stepped Asymmetric PCR Scheme

Figure 2:
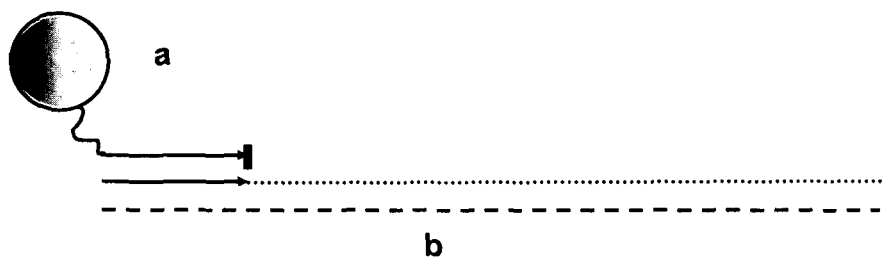
FIG. 2 is a diagrammatic representation of a mechanism for increased solid support priming using (B) ESP-PCR versus standard (A) SP-PCR. 'Aqueous' forward (arrow) and reverse primers are included in each reaction mix at non-limiting concentrations, along with solid support primer (sphere linked to an arrow). 'Aqueous' primers take part in conventional PCR to generate amplicons (dashed lines). Solid support primers also prime extension reactions during these cycles, resulting in the loading of product onto the solid support surface. However, in standard SP-PCR, solid support primer involvement is inhibited by competition with an 'aqueous' primer of matching sequence (A), to result in relatively poor amplicon loading. The vertical line in (A) indicates inhibited extension. ESP-PCR (B) avoids such inhibition by employing a nested solid support primer of relatively high $T_m$. Dotted lines represent extension events.
Figure 2:
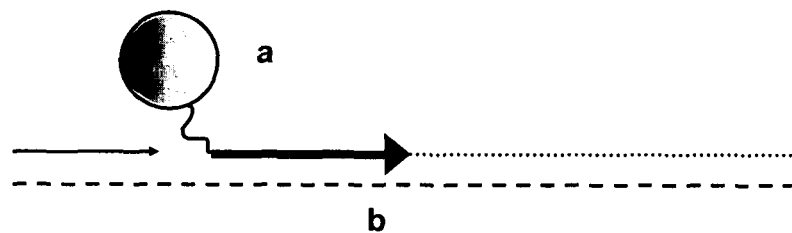

Enhanced Solid Phase-PCR (ESP-PCR) is a mechanism designed herein to combine the high sensitivity of uncompromised symmetric 'aqueous' PCR with efficient solid support loading. ESP-PCR alters the mechanism by which amplicon is loaded onto solid support by removing competition between 'aqueous' primer and solid support primer to increase solid support primer priming (FIG. 2). 'Aqueous' primer does not have to be limited, thus enabling a more sensitive system. Further, the primer design inherent to ESP-PCR offers the optional potential of applying latter thermal cycles at annealing temperatures permissive exclusively to solid support primer binding.

This Example details ESP-PCR performed using constant solid support material, primer surface density and 'linker' sequence with the scope and intention of dissecting out the mechanistic benefits of ESP-PCR over SP-PCR.

Oligonucleotides

Oligonucleotides were purchased from Integrated DNA Technologies (Coralville, USA). Template generation oligonucleotides and ESP-PCR and SP-PCR oligonucleotides are listed in below. The conjugation efficiency measurement oligonucleotide (Transprobe) sequence was: /5AmMC6/GTCCATAGCTGTCCTCCCT (SEQ ID NO:1). All oligonucleotide sequences are listed in the 5-prime to 3-prime direction. /5Phos/, /5AmMC6/, /5Acryd/ and /iAmMC6T/ indicate 5-prime phosphate, 5-prime amine modifier, 5-prime acrydite and internal amine modifier groups, respectively. Ngo, Ngps and Cto3 refer to *Neisseria gonorrhoea* opa, *Neisseria gonorrhoea* pilS and *Chlamydia trachomatis* cryptic plasmid orf3, respectively. Underlined regions indicate non-target 'linker' sequence included in the 5-prime portion of solid support primer to facilitate presentation of the target-specific portion during 'amplicon loading'. This 'linker' sequence, shared by SP-PCR and ESP-PCR solid support primers, was also used as the Transprobe hybridization target for the assessment of primer loading onto solid support following conjugation.

Oligonucleotide Conjugation to Silica Microspheres

Silica microspheres of 6.8 μm diameter (Bangs Laboratories, Fishers, USA) were functionalized with sulphydryl groups before being conjugated to oligonucleotides. Integrated DNA Technologies product literature details the reaction between a solid support thiol and 5-prime acrydite group modified oligonucleotides (available online at the website: http://scitools.idtdna.com/support/technical/TechnicalBulletinPDF/Strategies forAttachingOligonucleotidestoSolidSupports.pdf). Following conjugation, microspheres were processed by a series of five spin/wash steps to remove any unbound oligonucleotides prior to suspension in buffer to 1 mg/ml. Levels of conjugation of oligonucleotides to microspheres were assessed by mixing 1 μl of homogeneous microsphere suspension with 5 μl of 50 mM sodium chloride-containing buffer and 0.5 μl of 10 μM Alexafluor647-labeled Transprobe (at a ratio of 2:1 Total Transprobe:Alexafluor647-labeled Transprobe). Alexafluor647 was purchased from Molecular Probes (Mount Waverley, Australia). Hybridization mixes were subjected to the following 'hybridization' thermal profile: 90° C. for 30 seconds, followed by cooling at a rate of 1° C./10 seconds to 20° C. Following hybridization, 124 μl of buffer was added prior to analysis by FACSArray (Becton Dickinson, North Ryde, Australia). Data presented in this study derived from this streamlined assay protocol. Microspheres can be subjected to more rigorous washing post-PCR with the effect of lowering the background fluorescence for the 'no template controls', without altering the signal intensity for templated ESP-PCR or SP-PCR samples. Microspheres were assessed in triplicate, in parallel, on the same instrument run using voltage parameters as follows: FCS 550, SSC 400, Far Red 100, Yellow 650, NIR 200, Red 700, FCS threshold 20000. *.fcs files were analysed using FCS Express v.3 to determine median red fluorescence. Student's T-test was applied to demonstrate equal solid support primer-microsphere conjugation between ESP-PCR and SP-PCR target pairs.

Template Generation

*Chlamydia trachomatis* serovar E DNA was used to template a PCR using Cto3 template generation forward and reverse primers to yield amplicon which included the ESP-PCR/SP-PCR oligonucleotides target region. Amplicon was agarose gel purified using a Qiaquick (Registered) gel extraction kit (Qiagen, Doncaster, Australia). Yield was approximated by gel electrophoresis assessment of product against the Hyperladder IV DNA standard (Bioline, Alexandria, Australia). Similarly, *Neisseria gonorrhoea* ATCC strain 43069 was used to template PCRs to generate Ngo and Ngps targets using their respective target generation primers.

ESP-PCR and SP-PCR

All ESP-PCRs and SP-PCRs were performed in 20 μl reaction volumes using 1 unit HotStarTaq [Registered] (Qiagen, Doncaster, Australia). HotStarTaq (Registered) reaction buffer was supplemented with $Mg^{2+}$ and dNTPs (New England Biolabs, Genesearch, Arundel, Australia) to yield reaction concentrations of 2 mM and 200 μM, respectively. Included in reactions were 1 μl of 5 μM 'aqueous' forward primer, 1 μl of 5 μM 'aqueous' reverse primer (Alexafluor647-labeled with a total oligonucleotide:fluor-labeled oligonucleotide ratio of 2:1) and 1 μl of 1 mg/ml solid support primer-conjugated microsphere suspension. Microspheres conjugated to SP-PCR or ESP-PCR solid support primer were included in SP-PCR or ESP-PCR reactions, respectively. ESP-PCR and SP-PCR were performed in triplicate, in parallel, using the same master mixes. In each case, primers and microspheres were grouped according to target and template. Reactions included 40000 copies of Cto3, 40000 copies of Ngo or 400000 copies of Ngps templates, respectively. The thermal profile employed was as follows: 94° C. 15 minutes, followed by 30 cycles of [90° C. 30 seconds, 44° C. 1 minute, 72° C. 1 minute], followed by 5 cycles of [90° C., 44° C. 2 minutes, 72° C. 2 minutes].

Flow Cytometry Analysis of ESP-PCR and SP-PCR

Following solid phase PCR, the bottom 5 μl was transferred to 120 μl of buffer in a 96-well microtitre plate. *.fcs files were generated by FACSArray with the same instrument settings as described earlier. Median red fluorescence figures were determined using FCS Express v.3.

Gel Electrophoresis

Post-flow cytometry sampling, 8 μl of residual PCR products were analysed using 3% agarose/TAE gels against 1.5 μg New England Biolabs 100 bp ladder (Genesearch, Arundel, Australia).

Template Generation Oligonucleotides.

```
Cto3 template generation forward primer  GATGCGGAAAAAGCTTACCAG

Cto3 template generation reverse primer  GGGCTTAGAATCACCTTCTCG

Ngo template generation forward primer   GCGGATTAACAAAAATCAGGACAA

Ngo template generation reverse primer   TAATCTGCCGCTATCCTCCAG

Ngps template generation forward primer  TTTTTTGCCGGCGTGGCATCC

Ngps template generation reverse primer  ATCGATATATTATTTCCACCGGAAC
```

ESP-PCR and SP-PCR Oligonucleotides.

```
Cto3 'aqueous' forward primer        /5Phos/ACAGACCCTTCTCTAGGT

Cto3 'aqueous' reverse primer        /5AmMC6/AATTCTAATACGACTCACTATAGGGC
                                     TTTTGGGTGTGACTGTG Cto3 SP-PCR solid support primer     /5Acryd/AAT/iAmMC6T/AAAGGGAGGACAGCTAT
                                     GGACACAGACCCTTCTCTAGGT Cto3 ESP-PCR solid support primer    /5Acryd/AAT/iAmMC6T/AAAGGGAGGACAGCTAT
                                     GGACCACTAATAAAATTCAATGCAACGGGTTAT
                                     TCACTC Ngo 'aqueous' forward primer         /5Phos/GCCATATTGTGTTGAAACAC Ngo 'aqueous' reverse primer         /5AmMC6/AATTCTAATACGACTCACTATAGGGG
                                     TTTGACCGGTTAAAAAAGA Ngo SP-PCR solid support primer      /5Acryd/AAT/iAmMC6T/AAAGGGAGGACAGCTAT
                                     GGACGCCATATTGTGTTGAAACAC Ngo ESP-PCR solid support primer     /5Acryd/AAT/iAmMC6T/AAAGGGAGGACAGCTAT
                                     GGACCCCGATATAATCCGCCCTTCAACATCAGT
                                     G Ngps 'aqueous' forward primer        /5Phos/AATGAGGCAAATTAGGGCT Ngps 'aqueous' reverse primer        /5AmMC6/AATTCTAATACGACTCACTATAGGGC
                                     TTGCAAACCCTTAAAAGAC Ngps SP-PCR solid support primer     /5Acryd/AAT/iAmMC6T/AAAGGGAGGACAGCTAT
                                     GGACAATGAGGCAAATTAGGCCT Ngps ESP-PCR solid support primer    /5Acryd/AAT/iAmMC6T/AAAGGGAGGACAGCTAT
                                     GGACAAATCAAGCGGTAAGTGATTTCCCACGGC
```

Multiplex Assay for *Neisseria gonorrhoeae* and *Chlamydia trachomatis* Detection by ESP-PCR Ngo ESP-PCR and Cto3 ESP-PCR solid support primers listed above were conjugated to silica microspheres (Bangs Laboratories) of 5.6 µm diameter and 6.8 µm diameter, respectively, washed and pooled at 1 mg/ml per bead population. One microliter of pooled bead suspension was included in ESP-PCR reactions including *Neisseria gonorrhoeae* opa primers: 5'-GGCAACGMCGTACCGGTTT-3' (SEQ ID NO:20) and 5-primer Alexafluor647-labeled 5'-ACGTCACAGTTTACGCGTTTGACCGGT-TAAAAAAAGATTTTCAC-3' (SEQ ID NO:21) and *Chlamydia trachomatis* cryptic plasmid orf3 primers: 5'-AGCTTTTAACAACTTTCCAATCACTA-3' (SEQ ID 122) and 5-prime Alexafluor647-labeled 5'-ACGACTCAC-TATAGGGTCCCAGAGCTTTTGGGTGTG-3' (SEQ ID 123). *Neisseria gonorrhoea* ATCC strain 43069 genomic DNA or plasmid bearing the above listed (see Template Generation) *Chlamydia trachomatis* cryptic plasmid orf3-spanning amplicon region, with the inclusion of 5 ng Jurkat human genomic DNA were used to template PCRs versus just human genomic DNA or water controls. Reactions were performed in a total volume of 20 µl using two units of PlatinumTaq [Trademark] (Invitrogen) using the following cycling parameters: 94° C. 2 minutes, followed by 50 cycles of [90° C. 30 seconds, 55° C. 1 minute, 72° C. 1 minute], followed by 72° C. 5 minutes. Silica microspheres were spin/washed twice with buffer, prior to FACSArray analysis using the above listed instrument settings.

Following conjugation, microspheres were washed thoroughly prior to suspension in buffer to 1 mg/ml. Levels of conjugation of oligonucleotides to microspheres were assessed by hybridizing Alexafluor647(Molecular Probes)-labeled 'Transprobe' to solid support primer linker sequence followed by flow cytometry analysis. Microspheres were assessed in triplicate, in parallel, on the same instrument run using voltage parameters as follows: FCS 550, SSC 400, Far Red 100, Yellow 650, NIR 200, Red 700, FCS threshold 20000. *.fcs files were analyzed using FCS Express v.3 to determine median red fluorescence. Student's T-test was applied to demonstrate equal solid support primer-microsphere conjugation between ESP-PCR and SP-PCR target pairs (Ng opa, P=0.919; Ng pilS, P=0.759; CtCP orf3, P=0.829). As such, any observed increases in amplicon loading following the application of ESP-PCR versus SP-PCR would be due to improved solid support priming rather than differential solid support primer conjugation levels.

Comparative experiments between ESP-PCR and SP-PCR were performed in 20 µl reaction volumes using 1 unit HotStarTaq [Registered] (Qiagen). HotStarTaq (Registered) reaction buffer was supplemented with $Mg^{2+}$ and dNTPs (New England Biolabs) to yield reaction concentrations of 2 mM and 200 µM, respectively. Included in reactions were 1 µl of 5 µM 'aqueous' forward primer, 1 µl of 5 µM 'aqueous' reverse primer (Alexafluor647-labeled with a total oligonucleotide:fluor-labeled oligonucleotide ratio of 2:1) and 1 µl of 1 mg/ml solid support primer-conjugated microsphere suspension. Microspheres conjugated to ESP-PCR or SP-PCR solid support primer were included in ESP-PCR or SP-PCR reactions, respectively. ESP-PCR and SP-PCR were performed in triplicate, in parallel, using the same master mixes. In each case, primers and microspheres were grouped according to target and template (linear dsDNA including primer binding regions). Reactions included 40000 copies of

*Chlamydia trachomatis* cryptic plasmid or 13, 40000 copies of *Neisseria gonorrhoea* opa or 400000 copies of *Neisseria gonorrhoea* pilS templates, respectively, or no template controls (to demonstrate background fluorescent levels) and employed the following thermal profile: 94° C. 15 min, followed by 30 cycles of [90° C. 30 s, 44° C. 1 min, 72° C. 1 min], followed by 5 cycles of [90° C., 44° C. 2 min, 72° C. 2 min]. Following solid phase PCR, the bottom 5 μl was transferred to 120 μl of buffer in a 96-well microtiter plate. *.fcs files were generated by FACSArray with the same instrument settings as previously described. Median red fluorescence figures were determined using FCS Express v.3.

ESP-PCR resulted in markedly increased solid support amplicon loading versus SP-PCR across all three targets assessed (Table 3), with strong statistical significance: Ng opa (9.89-fold, P=0.00000661), Ng pilS (2.14-fold, P=0.001095) and CtCP orf3 (1.41-fold, P=0.000935). P values relate to the null hypothesis that there is no difference in amplicon loading between ESP-PCR and SP-PCR. Fold-increases refer to ESP-PCR RFU/SP-PCR RFU. Variation in fold-increase across targets was not unexpected owing to the inherent variations in hybridization efficiencies between oligonucleotides and the fact that complex competitive hybridization events are involved. Despite this variation, ESP-PCR was universally beneficial across the targets studied. Non-microsphere-bound 'aqueous' amplicons from the same reaction vessels as used for flow cytometry measurements were of equal yield across all targets following ESP-PCR versus SP-PCR as assessed by agarose gel electrophoresis. 'Aqueous' product yields were also identical with or without microspheres in the reaction mix to indicate that the silica microspheres conjugated to solid support primers did not compromise amplification efficiency. Post-ESP-PCR, solid support was thoroughly washed via multiple centrifugation and buffer exchange steps and used to template limited cycle 're-amplification' reactions including previously used 'aqueous' primers and an 'aqueous' version of solid support primer. Single band products of sizes corresponding to those expected of products derived from solid support primer and 'aqueous' reverse primer priming were observed upon gel electrophoresis to indicate that ESP-PCR solid support products were specific. Taken together, these data suggest that ESP-PCR was successful in achieving the dual goals of not compromising 'aqueous phase' amplification and increasing solid support surface loading with amplicon relative to standard SP-PCR, in a specific manner.

These observed benefits are due to loading mechanisms in which: (i) the effective concentration of solid support primer is increased by virtue of its relatively high $T_m$. Linear-After-The-Exponential-PCR (LATE-PCR) improves the generation of single-stranded products by Asymmetric PCR (Sanchez et al, *Proc. Natl. Acad. Sci. USA* 101:1933-1938, 2004). In this approach, a 'tighter binding', limited concentration primer was employed to increase its 'effective concentration' in the reaction, based on the relationship between primer $T_m$ and primer concentration described by the 'nearest-neighbour' formula (SantaLucia, *Proc. Natl. Acad. Sci. USA* 95:1460-1465, 1998). In ESP-PCR this principle is applied to the solid support primer. A 'tighter binding' solid support primer has an increased 'effective concentration' and improved kinetics of binding and priming. (ii) the solid support primer is nested with respect to its 'aqueous' counterpart. Since the solid support primer recognizes a different binding site to the 'aqueous' forward primer, direct competition for amplicon binding is removed. In ESP-PCR, unlike SP-PCR, in order for solid support priming to be inhibited by 'blocking' of the solid support primer binding site, it is necessary for 'aqueous' forward primer to bind to amplicon template and for polymerase to subsequently find and bind to this substrate, and for polymerization to ensue within a short space of time. In both standard SP-PCR and Asymmetric SP-PCR, simply binding of aqueous primer to its primer binding site is sufficient to inhibit solid support priming. In the method of PCR Clamping, amplification is specifically blocked by the inclusion of internal (nested) peptide nucleic acid or locked nucleic acid probes (Dominguez and Kolodney, *Oncogene* 24:6830-6834, 2005; Orum et al, *Nucleic Acids Res.* 21:5332-5336, 1993). Analagous to solid support primer of ESP-PCR, blocking probes of the PCR Clamping approach bind to amplicon before primer binding and polymerization have had a chance to occur.

Still applying the ESP-PCR principles, using 'aqueous' primers and thermocycling parameters five *Neisseria gonorrhoea* genomes and five *Chlamydia trachomatis* genome equivalents were detected per single multiplex ESP-PCR reaction by FACSArray. This approach used solid support primers conjugated to silica microspheres of different diameters to facilitate discrimination by flow cytometry. Reactions were templated with *Neisseria gonorrhoea* genomic DNA and plasmid containing *Chlamydia trachomatis* target region with the inclusion of Jurkat human genomic DNA versus just Jurkat human genomic DNA or water.

TABLE 3

Solid support amplicon loading versus SP-PCR

| Target | No template control SP-PCR | SP-PCR | No template control ESP-PCR | ESP-PCR |
| --- | --- | --- | --- | --- |
| Ng opa | 37.18 RFU | 52.98 RFU (1.12) | 44.91 RFU | 523.74 RFU (15.24) |
| Ng pilS | 40.68 RFU | 74.36 RFU (1.78) | 39.60 RFU | 159.09 RFU (9.92) |
| CtCP orf3 | 41.79 RFU | 209.84 RFU (5.10) | 38.89 RFU | 295.39 RFU (8.33) |

Increased loading of silica microspheres with red fluorescence-labeled amplicon following ESP-PCR versus SP-PCR. RFU refers to relative fluorescence units. Numbers in brackets represent the standard error of the mean of triplicate series ESP-PCR is compared to SP-PCR, employing silica microspheres as the solid support, across a range of clinically relevant targets: *Neisseria gonorrhoea* opa (Ng opa) and pilS (Ng pilS) and *Chlamydia trachomatis* cryptic plasmid orf3

(CtCP orf3) [McLeod et al, *Infection and Immunity* 67:3469-3480, 1999; Comanducci et al, *J. Gen Microbiol* 139:1083-1092, 1993].

Briefly, ESP-PCR and SP-PCR solid support primers were prepared as follows: silica microspheres of 6.8 μm diameter (Bangs Laboratories) were functionalized with sulphydryl groups before being conjugated to acrydite group modified oligonucleotides.

EXAMPLE 3

'Thermally Stepped' or 'Unstepped' ESP-PCR and SP-PCR

Thermally stepped or non-stepped protocols were set up in parallel for Chlamydia trachomatis cryptic plasmid orf3target as part of the experiment described in Example 2. For 'non-stepped' PCR, thermal profile 44-44 was employed: 94° C. 15 mins followed by [30 cycles of 90° C. 30 seconds, 44° C. 1 minute, 72° C. 1 minute] followed by [5 cycles of 90° C., 44° C. 2 minutes, 72° C. 2 minutes]. For 'Stepped' PCR, thermal profile 44-60 was employed: 94° C. 15 mins followed by [30 cycles of 90° C. 30 seconds, 44° C. 1 minute, 72° C. 1 minute] followed by [5 cycles of 90° C., 60° C. 2 minutes, 72° C. 2 minutes]. The results are shown in Table 4.

Following solid phase PCR, the bottom 5 μl was transferred to 120 μl buffer in a 96-well microtitre plate. *.fcs files were generated by employing a BD FACSArray using the same instrument settings as described in Example 2. Median red fluorescence figures were determined using FCS Express v.3.

Post-flow cytometric sampling, 8 μl of residual PCR products were run on 3% w/v agarose/TAE gels against 1.5 μg New England Biolabs 100 bp ladder (Genesearch, Arundel, Australia).

The potential benefits of an optimal 'thermal step' as part of the ESP-PCR protocol were studied (44-60). The higher annealing temperature during latter PCR cycles improved surface loading of *Chlamydia trachomatis* cryptic plasmid orf3 amplicon ((1.15-fold increase). (Student's T-test, probability that the results are the same: P=0.0124) over a 'non-stepped' thermal ESP-PCR protocol (44-44).

Gel electrophoretic profiles of non-microsphere-bound amplicons from the same reaction vessels as assessed by flow cytometry. In all cases, comparable yields of 'aqueous phase' PCR products were observed to suggest that differences in microsphere amplicon loading were not influenced by 'aqueous phase' PCR product yield. There were no discernable differences between aqueous product yields with or without microspheres included in the reaction mix.

Increased loading of silica microspheres with red fluorescence-labeled amplicon following 'thermally stepped' ESP-PCR versus 'unstepped' ESP-PCR. Ct orf3 refers to the *Chlamydia trachomatis* cryptic plasmid orf3. RFU refers to relative fluorescence units. Numbers in brackets represent the standard error of the mean of triplicate series.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Aono et al, Japanese Patent Publ. No. JP 4-262799
Comanducci et al, *J. Gen Microbiol* 139:1083-1092, 1993
Dieffenbach (Ed), *PCR Primer: A Laboratory Manual*, 2$^{nd}$ Edition, Cold Spring Harbor Press, New York, 2003
Dominguez and Kolodney, *Oncogene* 24:6830-6834, 2005
Eckstein (Ed), *Oligonucleotides and Analogs: A Practical Approach*, Oxford University Press, New York, 1991
Gait (Ed), *Oligonucleotide Synthesis: A Practical Approach*, IRL Press, Oxford, 1984
Gyllensten and Erlich, *Proc. Natl. Acad. Sci. USA* 85:7652-7656 1998
Higuchi et al, *Nucl. Acids Res.* 25:5685, 1989
Kaltenboeck et al, *Biotechniques*. 12:164-171, 1992
Kanehisa *Nucleic Acids Res.* 12:203, 1984
Kornberg and Baker, *DNA Replication*, Second Edition, W.H. Freeman, New York, 1992
Lehninger, Biochemistry, Second Edition, Worth Publishers, New York, 1975
McLeod et al, *Infection and Immunity* 67:3469-3480, 1999
McPherson et al. (Eds), *PCR: A Practical Approach* and *PCR2: A Practical Approach*, IRL Press, Oxford, 1991
McPherson et al. (Eds), *PCR: A Practical Approach* and *PCR2: A Practical Approach*, IRL Press, Oxford, 1995
Mackay et al, *Nucleic Acids Research*, 30:1292-1305, 2002
Orum et al, *Nucleic Acids Res.* 21:5332-5336, 1993
Sanchez et al, *Proc. Natl. Acad. Sci. USA* 101:1933-1938, 2004
SantaLucia, *Proc. Natl. Acad. Sci. USA* 95:1460-1465, 1998
Schena (Ed), Microarrays: A Practical Approach (IRL Press, Oxford, 2000); Southern, *Current Opin. Chem. Biol.*, 2: 404-410, 1998
Shchepinov et al, *Nuc. Acids. Res.* 25:4447-4454 1997
Strachan and Read, *Human Molecular Genetics*, Second Edition, Wiley-Liss, New York, 1999
Tecott et al, U.S. Pat. No. 5,168,038

TABLE 4

'Thermally stepped' or 'unstepped' ESP-PCR and SP-PCR

| Target (thermal protocol) | No template control SP-PCR | SP-PCR | No template control ESP-PCR | ESP-PCR |
|---|---|---|---|---|
| Ct orf3 44-44 ('unstepped') | 41.79 RFU | 209.84 RFU (5.10) | 38.89 RFU | 295.39 RFU (8.33) |
| Ct orf3 44-60 ('stepped') | 42.17 RFU | 246.79 RFU (15.08) | 39.24 RFU | 339.93 RFU (6.06) |

The invention claimed is:

1. A method for solid phase amplification of a polynucleotide molecule sequence in a reaction vessel comprising:
   (a) a) combining in said reaction vessel:
      i) a target DNA molecule that comprises the polynucleotide molecule sequence,
      ii) a pair of aqueous forward and reverse primers that bind to 5' and 3' ends of the polynucleotide sequence, respectively, and
      iii) a solid support conjugated to a solid support primer, wherein the solid support primer comprises a target-specific sequence that has at least 80% sequence identity to the forward primer and a 3' sequence extension that extends beyond the sequence of the forward primer, wherein the target-specific sequence hybridizes to the target DNA molecule, and wherein the Tm of the solid support primer is higher than the Tm of the aqueous forward primer; and
   (b) amplifying the polynucleotide molecule sequence by polymerase chain reaction, wherein:
      i) during a plurality of first thermal cycles, annealing conditions are permissive to the forward primer, the reverse primer and the solid support primer, and
      ii) during a plurality of second thermal cycles conducted after said first thermal cycles, annealing steps have a raised temperature compared to the first thermal cycles, such that, during the second thermal cycles, the solid support primer anneals to target efficiently, but the aqueous forward primer does not, wherein solid phase amplification of the polynucleotide molecule sequence is favored during the second thermal cycles.

2. The method of claim 1 wherein an amplified polynucleotide molecule is immobilized to the solid support, which is then subjected to denaturing conditions to generate immobilized single stranded polynucleotide molecules and aqueous phase single stranded polynucleotide molecules.

3. The method of claim 1, wherein amplification results in generation of a single-stranded polynucleotide, further comprising isolating the single stranded polynucleotide through phase separation.

4. The method of claim 1, wherein amplification results in generation of a single-stranded polynucleotide, and wherein the single stranded polynucleotide is immobilized to the solid support and comprises a label capable of generating a detectable signal.

5. The method of claim 1 wherein the polynucleotide to be amplified comprises either a recessed 5' end or a blunt end which is incubated with a 5' to 3' exonuclease to generate a single stranded polynucleotide template.

6. The method of claim 1 wherein the solid support primer is conjugated to the solid support by a linking sequence.

7. The method of claim 1, wherein the solid support is a micro sphere or a microbead.

8. A method of detecting and distinguishing analytes from multiple genomic sources comprising:
   amplifying different polynucleotides from the multiple genomic sources, wherein each of the different polynucleotides are amplified by the method of claim 1, and wherein each of the different polynucleotides are amplified by a different pair of aqueous forward and reverse primers, as recited in claim 1, and by a different solid support primer, as recited in claim 1, wherein the different solid support primers are bound to different, identifiable micro spheres or microbeads; and detecting and distinguishing each of the amplified different polynucleotides on each of the different identifiable micro spheres or a microbeads.

9. The method of claim 8, wherein the different identifiable microspheres or a microbeads are identifiable on the basis of the microspheres or a microbeads having different diameters.

* * * * *

SEQUENCE LISTING

<160> NUMBER OF SEQ ID NOS: 23

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide (Transprobe)

<400> SEQUENCE: 1
gtccatagct gtcctccct                                              19

<210> SEQ ID NO 2
<211> LENGTH: 21
<212> TYPE: DNA
<213> ORGANISM: Artificial Sequence
<220> FEATURE:
<223> OTHER INFORMATION: Cto3 template generation forward primer

<400> SEQUENCE: 2
gatgcggaaa aagcttacca g                                           21

<210> SEQ ID NO 3
<211> LENGTH: 21
<212> TYPE: DNA
<213> ORGANISM: Artificial Sequence
<220> FEATURE:
<223> OTHER INFORMATION: Cto3 template generation reverse primer

<400> SEQUENCE: 3
gggcttagaa tcaccttctc g                                           21

<210> SEQ ID NO 4
<211> LENGTH: 24
<212> TYPE: DNA
<213> ORGANISM: Artificial Sequence
<220> FEATURE:
<223> OTHER INFORMATION: Ngo template generation forward primer

<400> SEQUENCE: 4
gcggattaac aaaaatcagg acaa                                        24

<210> SEQ ID NO 5
<211> LENGTH: 21
<212> TYPE: DNA
<213> ORGANISM: Artificial Sequence
<220> FEATURE:
<223> OTHER INFORMATION: Ngo template generation reverse primer

<400> SEQUENCE: 5
taatctgccg ctatcctcca g                                           21

<210> SEQ ID NO 6
<211> LENGTH: 21
<212> TYPE: DNA
<213> ORGANISM: Artificial Sequence
<220> FEATURE:
<223> OTHER INFORMATION: Ngps template generation forward primer

<400> SEQUENCE: 6 tttttgccg gcgtggcatc c                                            21

<210> SEQ ID NO 7
<211> LENGTH: 25
<212> TYPE: DNA
<213> ORGANISM: Artificial Sequence

```
<220> FEATURE:
<223> OTHER INFORMATION: Ngps template generation reverse primer

<400> SEQUENCE: 7
atcgatatat tatttccacc ggaac                                           25

<210> SEQ ID NO 8
<211> LENGTH: 18
<212> TYPE: DNA
<213> ORGANISM: Artificial Sequence
<220> FEATURE:
<223> OTHER INFORMATION: Cto3 'aqueous' forward primer

<400> SEQUENCE: 8 acagacccttt ctctaggt                                                  18

<210> SEQ ID NO 9
<211> LENGTH: 43
<212> TYPE: DNA
<213> ORGANISM: Artificial Sequence
<220> FEATURE:
<223> OTHER INFORMATION: Cto3 'aqueous' reverse primer

<400> SEQUENCE: 9
aattctaata cgactcacta tagggctttt gggtgtgact gtg                       43

<210> SEQ ID NO 10
<211> LENGTH: 43
<212> TYPE: DNA
<213> ORGANISM: Artificial Sequence
<220> FEATURE:
<223> OTHER INFORMATION: Cto3 SP-PCR solid support primer

<400> SEQUENCE: 10
aattaaaggg aggacagcta tggacacaga cccttctcta ggt                       43

<210> SEQ ID NO 11
<211> LENGTH: 60
<212> TYPE: DNA
<213> ORGANISM: Artificial Sequence
<220> FEATURE:
<223> OTHER INFORMATION: Cto3 ESP-PCR solid support primer

<400> SEQUENCE: 11
aattaaaggg aggacagcta tggaccacta ataaaattca atgcaacggg ttattcactc     60

<210> SEQ ID NO 12
<211> LENGTH: 20
<212> TYPE: DNA
<213> ORGANISM: Artificial Sequence
<220> FEATURE:
<223> OTHER INFORMATION: Ngo 'aqueous' forward primer

<400> SEQUENCE: 12
gccatattgt gttgaaacac                                                 20

<210> SEQ ID NO 13
<211> LENGTH: 46
<212> TYPE: DNA
<213> ORGANISM: Artificial Sequence
<220> FEATURE:
<223> OTHER INFORMATION: Ngo 'aqueous' reverse primer

<400> SEQUENCE: 13
aattctaata cgactcacta tagggggtttg accggttaaa aaaga                    46
```

```
<210> SEQ ID NO 14
<211> LENGTH: 45
<212> TYPE: DNA
<213> ORGANISM: Artificial Sequence
<220> FEATURE:
<223> OTHER INFORMATION: Ngo SP-PCR solid support primer

<400> SEQUENCE: 14
aattaaaggg aggacagcta tggacgccat attgtgttga aacac              45

<210> SEQ ID NO 15
<211> LENGTH: 55
<212> TYPE: DNA
<213> ORGANISM: Artificial Sequence
<220> FEATURE:
<223> OTHER INFORMATION: Ngo ESP-PCR solid support primer

<400> SEQUENCE: 15
aattaaaggg aggacagcta tggaccccga tataatccgc ccttcaacat cagtg   55

<210> SEQ ID NO 16
<211> LENGTH: 19
<212> TYPE: DNA
<213> ORGANISM: Artificial Sequence
<220> FEATURE:
<223> OTHER INFORMATION: Ngps 'aqueous' forward primer

<400> SEQUENCE: 16
aatgaggcaa attaggcct                                           19

<210> SEQ ID NO 17
<211> LENGTH: 45
<212> TYPE: DNA
<213> ORGANISM: Artificial Sequence
<220> FEATURE:
<223> OTHER INFORMATION: Ngps 'aqueous' reverse primer

<400> SEQUENCE: 17
aattctaata cgactcacta tagggcttgc aaacccttaa aagac              45

<210> SEQ ID NO 18
<211> LENGTH: 44
<212> TYPE: DNA
<213> ORGANISM: Artificial Sequence
<220> FEATURE:
<223> OTHER INFORMATION: Ngps SP-PCR solid support primer

<400> SEQUENCE: 18
aattaaaggg aggacagcta tggacaatga ggcaaattag gcct               44

<210> SEQ ID NO 19
<211> LENGTH: 54
<212> TYPE: DNA
<213> ORGANISM: Artificial Sequence
<220> FEATURE:
<223> OTHER INFORMATION: Ngps ESP-PCR solid support primer

<400> SEQUENCE: 19
aattaaaggg aggacagcta tggacaaatc aagcggtaag tgatttccca cggc    54

<210> SEQ ID NO 20
<211> LENGTH: 19
<212> TYPE: DNA
<213> ORGANISM: Artificial Sequence
<220> FEATURE:
<223> OTHER INFORMATION: Neisseria gonorrhoeae opa primer
```

-continued

```
<400> SEQUENCE: 20
ggcaacgmcg taccggttt                                                    19

<210> SEQ ID NO 21
<211> LENGTH: 44
<212> TYPE: DNA
<213> ORGANISM: Artificial Sequence
<220> FEATURE:
<223> OTHER INFORMATION: Alexafluor647-labeled 5' primer

<400> SEQUENCE: 21
acgtcacagt ttacgcgttt gaccggttaa aaaaagattt tcac                        44

<210> SEQ ID NO 22
<211> LENGTH: 26
<212> TYPE: DNA
<213> ORGANISM: Artificial Sequence
<220> FEATURE:
<223> OTHER INFORMATION: Chlamydia trachomatis cryptic plasmid orf3
      primer

<400> SEQUENCE: 22
agcttttaac aactttccaa tcacta                                            26

<210> SEQ ID NO 23
<211> LENGTH: 36
<212> TYPE: DNA
<213> ORGANISM: Artificial Sequence
<220> FEATURE:
<223> OTHER INFORMATION: Alexafluor647-labeled 5' primer

<400> SEQUENCE: 23
acgactcact atagggtccc agagcttttg ggtgtg                                 36
```